(12) United States Patent
Shi et al.

(10) Patent No.: US 10,721,826 B2
(45) Date of Patent: Jul. 21, 2020

(54) MEDICAL DEVICES

(71) Applicant: Medtronic, Inc., Minneapolis, MN (US)

(72) Inventors: Songhua Shi, Tempe, AZ (US); Darrin T. Schauble, Phoenix, AZ (US); Rachel M. Day, Tempe, AZ (US)

(73) Assignee: Medtronic, Inc., Minneapolis, MN (US)

( * ) Notice: Subject to any disclaimer, the term of this patent is extended or adjusted under 35 U.S.C. 154(b) by 182 days.

(21) Appl. No.: 15/968,928

(22) Filed: May 2, 2018

(65) Prior Publication Data

US 2019/0343011 A1 Nov. 7, 2019

(51) Int. Cl.
| | | |
|---|---|---|
| *H05K 5/00* | (2006.01) | |
| *H01R 12/57* | (2011.01) | |
| *H05K 5/06* | (2006.01) | |
| *A61B 5/0492* | (2006.01) | |
| *H05K 5/02* | (2006.01) | |

(52) U.S. Cl.
CPC ......... *H05K 5/0069* (2013.01); *A61B 5/0492* (2013.01); *H01R 12/57* (2013.01); *H05K 5/0247* (2013.01); *H05K 5/064* (2013.01); *A61B 2562/125* (2013.01)

(58) Field of Classification Search
CPC ..... H05K 5/0069; A61B 5/0492; H01R 12/57
See application file for complete search history.

(56) References Cited

U.S. PATENT DOCUMENTS

| | | | | |
|---|---|---|---|---|
| 2006/0110599 A1* | 5/2006 | Honma | ..................... | B32B 5/10 428/413 |
| 2011/0048770 A1* | 3/2011 | Reiterer | ............... | A61N 1/3754 174/152 GM |
| 2011/0189440 A1* | 8/2011 | Appleby | ................... | B22C 9/04 428/156 |
| 2012/0094106 A1* | 4/2012 | Honma | ..................... | B32B 5/10 428/299.1 |
| 2012/0197368 A1* | 8/2012 | Reisinger | ............. | A61N 1/3754 607/116 |
| 2012/0253270 A1* | 10/2012 | Steinbach | ............ | A61K 9/0024 604/67 |
| 2012/0290021 A1* | 11/2012 | Saurkar | .............. | A61N 1/37205 607/2 |
| 2013/0131257 A1* | 5/2013 | Sharma | ................... | C08L 67/02 524/539 |
| 2013/0184796 A1* | 7/2013 | Marzano | ................ | H01G 4/005 607/116 |

(Continued)

*Primary Examiner* — Christopher A Flory (57) ABSTRACT

In some examples, a medical device may include circuitry on a circuit board, a casing, and a fill material at least partially within the casing. The casing may receive the circuit board and surround at least a portion of the circuit board. The casing may define an aperture configured to allow one or more electrical connectors of the circuit board to extend through the aperture for one or more electrical connections with one or more components outside of the casing. An outer surface of the casing may define a first portion of an outer surface of the medical device. The casing may comprise a material having a first melting temperature. The fill material may define a second portion of the outer surface of the medical device and may have a second melting temperature that is lower than the first melting temperature.

23 Claims, 7 Drawing Sheets

(56) References Cited

U.S. PATENT DOCUMENTS

| | | | | |
|---|---|---|---|---|
| 2013/0184797 | A1* | 7/2013 | Tang | A61N 1/08 607/116 |
| 2013/0230424 | A1* | 9/2013 | Reiterer | A61N 1/3754 419/8 |
| 2013/0286537 | A1* | 10/2013 | Brendel | H01G 4/228 361/302 |
| 2014/0161973 | A1* | 6/2014 | Tang | A61N 1/08 427/125 |
| 2014/0163664 | A1* | 6/2014 | Goldsmith | A61B 17/00491 623/1.11 |
| 2014/0343648 | A1* | 11/2014 | Specht | A61N 1/3754 607/116 |
| 2015/0134039 | A1* | 5/2015 | Marzano | C22C 29/12 607/116 |
| 2015/0306376 | A1* | 10/2015 | Novotny | A61N 1/05 607/116 |
| 2016/0008595 | A1* | 1/2016 | Stevenson | H01G 4/12 361/302 |
| 2016/0082502 | A1* | 3/2016 | Appleby | B22C 9/04 164/369 |
| 2016/0263384 | A1* | 9/2016 | Stevenson | A61N 1/3754 |
| 2017/0080239 | A1* | 3/2017 | Seitz | H01G 2/103 |
| 2018/0067003 | A1* | 3/2018 | Michiwaki | G01L 5/243 |
| 2018/0126176 | A1* | 5/2018 | Seitz | H01B 17/303 |
| 2018/0197661 | A1* | 7/2018 | Seitz | H01B 17/30 |
| 2018/0243527 | A1* | 8/2018 | Zapol | A61M 16/107 |
| 2018/0304084 | A1* | 10/2018 | Stevenson | A61N 1/05 |
| 2018/0361164 | A1* | 12/2018 | Stevenson | H01G 4/12 |
| 2019/0054274 | A1* | 2/2019 | King | A61B 5/062 |
| 2019/0244729 | A1* | 8/2019 | Seitz | A61N 1/3754 |
| 2019/0247050 | A1* | 8/2019 | Goldsmith | A61B 17/12181 |
| 2020/0030613 | A1* | 1/2020 | Stevenson | A61N 1/3754 |

* cited by examiner

MEDICAL DEVICES

TECHNICAL FIELD

This disclosure relates to medical devices and, more particularly, to techniques for making medical devices and medical devices made using such techniques.

BACKGROUND

Medical devices including one or more electronic components have been proposed for use with various medical procedures. For example, in some cases, a medical device may be used to monitor a physiological parameter of a subject and/or control delivery of a therapy to the subject. Such medical devices typically include a printed circuit board, which may include integrated and/or discrete electronic components, and a power source. Size, shape, biocompatibility, and protection of medical device components from moisture are considerations when determining how to package components into a medical device.

SUMMARY

In some aspects, this disclosure describes example medical devices that each include a circuit board, circuitry on the circuit board that is configured to monitor a physiological parameter of a subject and/or control delivery of a therapy to the subject, a casing defining a first portion of an outer surface of the medical device, and a fill material, at least a portion of the fill material being within the casing, the fill material defining a second portion of the outer surface of the medical device. The circuit board may define at least two sides with at least one side including one or more electrical connectors. The casing may be defined to receive and surround at least a portion of the circuit board with a side of the circuit board including the one or more electrical connectors facing the casing. The casing may define an aperture configured to allow the one or more electrical connectors to extend through the aperture to electrically connect with one or more components outside of the casing.

In some examples, the casing may define one or more internal structures, such as one or more protrusions protruding inwardly from an inner surface of the casing, configured to support the circuit board after insertion of the circuit board into the casing, and before and during insertion of the fill material into the casing. In some examples, the one or more internal structures are configured to maintain a gap between at least one portion of a side of the circuit board and at least one portion of the casing during insertion of the fill material to allow for at least some of the fill material to be placed between the at least one portion of the side of the circuit board and the at least one portion of the casing. In some examples, the one or more internal structures may include an aperture wall defining at least a portion of the aperture.

In some examples, the casing may comprise a material having a first melting temperature and the fill material may have a second melting temperature that is lower than the first melting temperature. Thus, the fill material may be inserted around the circuit board without melting the casing. In this manner, the casing may support the circuit board during insertion of the fill material such that heat and/or force applied to the circuit board during insertion of the fill material does not warp the circuit board or the casing.

In some examples, a medical device comprises a circuit board, circuitry on the circuit board, a casing, and a fill material. The circuit board has a first side and a second side opposite the first side. The first side includes one or more electrical connectors. The circuitry on the circuit board is configured to at least one of monitor a physiological parameter of a subject or control delivery of a therapy to the subject. The casing is configured to receive the circuit board with the first side of the circuit board facing the casing and surround at least a portion of the circuit board. The casing defines an aperture configured to allow the one or more electrical connectors to extend through the aperture for one or more electrical connections between the one or more electrical connectors of the circuit board and one or more components outside of the casing. An outer surface of the casing defines a first portion of an outer surface of the medical device. The casing comprises a material having a first melting temperature. At least a portion of the fill material is within the casing. The fill material covers at least a portion of the first side of the circuit board and at least a portion of the second side of the circuit board. The fill material defines a second portion of the other surface of the medical device. The fill material has a second melting temperature that is lower than the first melting temperature.

In additional examples, a method of manufacturing a medical device, comprising a circuit board, circuitry on the circuit board, a casing and a fill material, comprises inserting the circuit board into the casing and inserting a at least a portion of a fill material into the casing. The circuit board has a first side and a second side opposite the first side. The first side includes one or more electrical connectors. Circuitry on the circuit board is configured to monitor a physiological parameter of a subject or control delivery of a therapy to the subject. The casing is configured to receive the circuit board with the first side of the circuit board facing the casing and surround at least a portion of the circuit board. The casing defines an aperture configured to allow the one or more electrical connectors to extend through the aperture for one or more electrical connections between the one or more electrical connectors of the circuit board and one or more components outside of the casing. An outer surface of the casing defines a first portion of an outer surface of the medical device. The casing comprises a material having a first melting temperature. The fill material does not extend over the outer surface the casing. The fill material defines a second portion of the outer surface of the medical device. The fill material has a second melting temperature that is lower than the first melting temperature.

In further examples, a medical device comprises a circuit board, circuitry on the circuit board, a casing, and a fill material. The circuit board has a first side and a second side opposite the first side. The first side includes one or more electrical connectors. The circuitry is configured to at least one of monitor a physiological parameter of a subject or control delivery of a therapy to the subject. The casing is configured to receive the circuit board with the first side of the circuit board facing the casing and surround at least a portion of the circuit board. The casing defines an aperture configured to allow the one or more electrical connectors to extend through the aperture for one or more electrical connections between the one or more electrical connectors of the circuit board and one or more components outside of the casing. An outer surface of the casing defines a first portion of an outer surface of the medical device. The casing defines one or more protrusions protruding inwardly from an inner surface of the casing and configured to support the circuit board after insertion of the circuit board into the casing and before insertion of a fill material within the casing. The casing comprises a material having a first melting temperature. At least a portion of the fill material is within the casing. The fill material covers at least a portion of the first side of the circuit board and at least a portion of the second side of the circuit board. The fill material defines a second portion of the other surface of the medical device. The fill material has a second melting temperature that is lower than the first melting temperature.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

In some examples, a medical device ("device") described herein includes circuitry on a circuit board, a casing configured do receive the circuit board, and fill material within the casing and covering at least a portion of the circuit board. The casing may define one or more apertures configured to allow one or more components of the circuit board, such as electrical connectors and/or a switch, to extend outside of the casing. The casing may include one or more internal structures configured to support the circuit board after the circuit board is inserted into the casing and before and during insertion of the fill material into the casing. In some examples, the fill material does not extend over an outer surface of the casing such that the casing may define a first portion of an outer surface of the device, while the fill material defines a second portion of the outer surface.

A casing including internal structures configured to support a circuit board within the casing before and during insertion of fill material within the casing and around the circuit board may avoid unwanted bending of circuit board and/or warping of the device upon cooling of the fill material.

Having a casing that defines at least a portion of an outer surface of the device may also provide certain advantages. For example, the casing may provide a cost-effective protective outer surface that is more durable, water proof, and/or water resistant than an outer surface including, for example, only fill material. Additionally, the casing may include one or more markings that may, for example, be used to identify the casing during and after assembly of the device to facilitate tracking of the casing and device during and after manufacture. Markings may also include, for example, a logo and/or regulatory, standards, and/or instructional information.

Figure 1A:
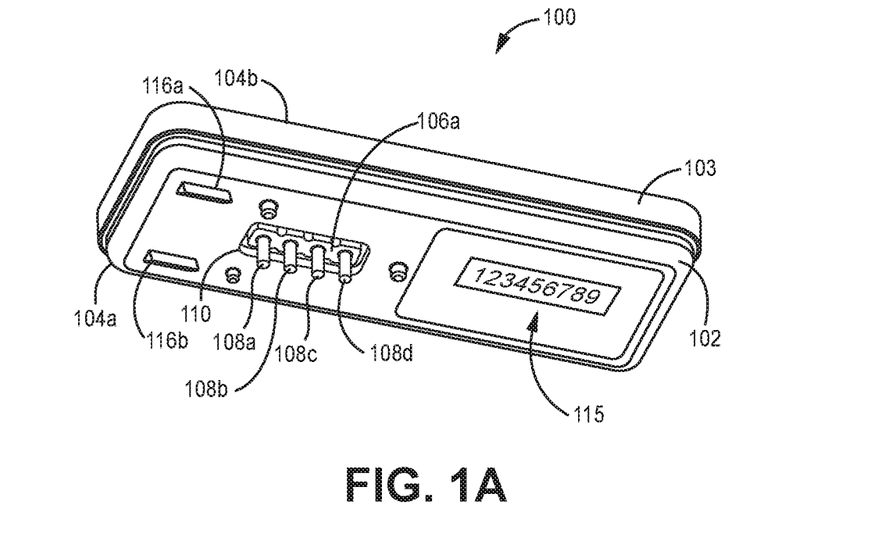
FIGS. 1A and 1B are conceptual perspective views showing opposite sides of an example medical device.
Figure 1B:
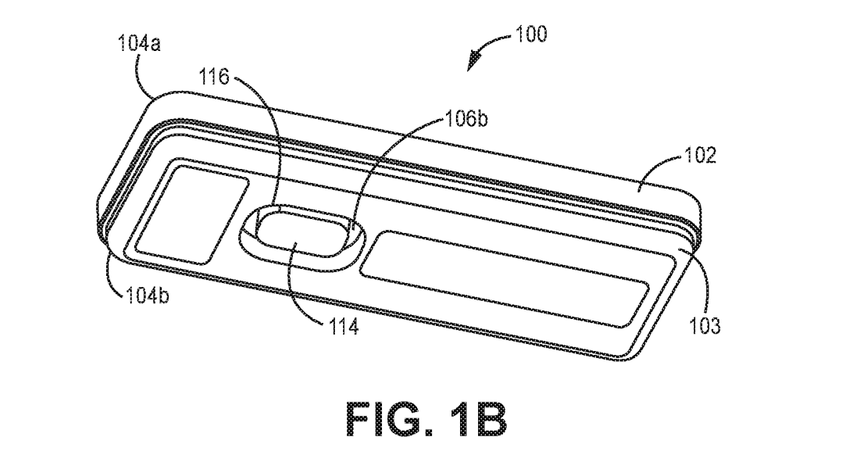
Figure 1C:
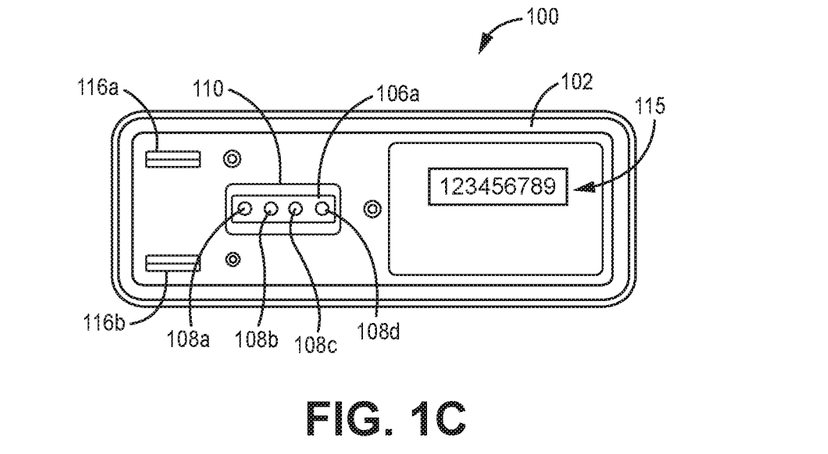
FIGS. 1C and 1D are conceptual side views showing opposite sides of the example medical device of FIGS. 1A and 1B.
Figure 1D:
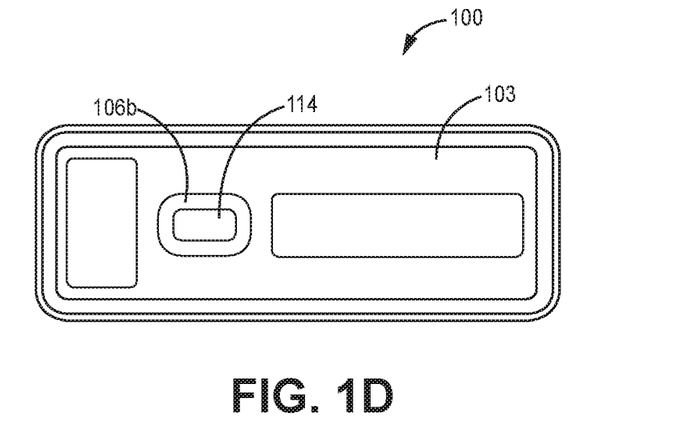

FIGS. 1A and 1B are conceptual perspective views showing opposite sides of an example medical device 100. FIGS. 1C and 1D are conceptual side views showing opposite sides of medical device 100 of FIGS. 1A and 1B. In some examples, medical device 100 may include a casing 102 defining a first portion 104a of an outer surface 104 of medical device 100, a circuit board 106 received within casing 102 (shown and described in further detail below with reference to FIGS. 2A and 2B), an overmolding 103 formed from a fill material and defining a second portion 104b of the outer surface 104 of medical device 100, as well as fill material (not shown in FIG. 1A) within the casing 102. Circuit board 106 may include one or more electrical connectors 108a-108d (collectively "electrical connector(s) 108") and casing 102 may define an aperture 110 configured to allow electrical connectors 108 to extend through aperture 110. In some examples, casing 102 may include plastic material, including polycarbonate, Nylon, co-polyester, cyclo olefin copolymer, acrylonitrile-butadiene-styrene (ABS), and/or polycarbonate acrylonitrile-butadiene-styrene (PCABS), ceramic, metal, and/or any other suitable material.

Figure 2A:
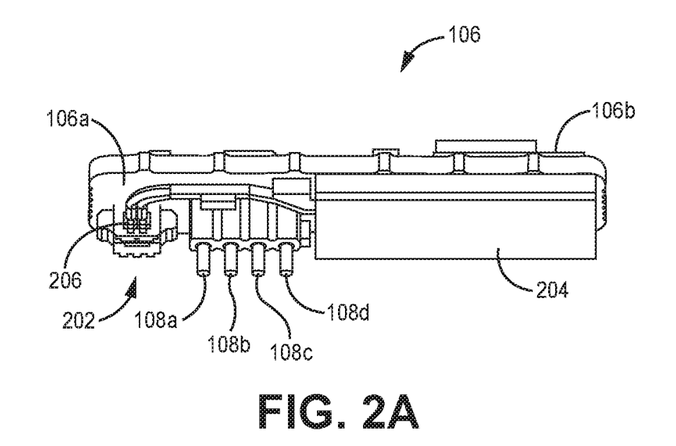
FIGS. 2A and 2B are conceptual perspective views of the circuit board of the medical device of FIGS. 1A-1D.
Figure 2B:
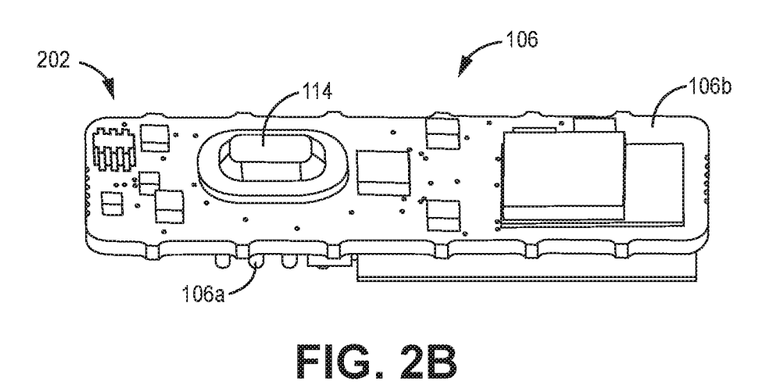

In some examples, medical device 100 may include circuit board 106, described in further detail below with reference to FIGS. 2A and 2B. In some examples, circuitry on circuit board 106 may be configured to monitor a physiological parameter of a subject and/or control delivery of a therapy to the subject. In some examples, circuit board 106 may have a first side 106a and a second side 106b opposite side 106a. FIGS. 1A and 1C show a portion of side 106a of circuit board 106. In some examples, side 106a of circuit board 106 may include one or more electrical connectors 108. FIGS. 1B and 1D show a portion of side 106b of circuit board 106. In some examples, side 106b of circuit board 106 may include a switch 114. In some examples, switch 114 may be substantially aligned with electrical connectors 108, which may allow for distribution of forces applied by mold tooling on the circuit board 106 during, for example, a molding process to apply fill material. Electrical connectors 108 may include one or more pin connectors. Electrical connectors 108 may be soldered to circuit board 106 or otherwise connected to circuit board 106 in any suitable way. In some examples, electrical connectors 108 may be spring loaded, as described in greater detail below. In some examples, electrical connectors 108 may conduct electrical inputs into or out of medical device 100 to, for example, detect electrical signals from the human body and/or provide electrical stimulus to the body. Alternatively or in addition, electrical connectors 108 may also be used for manufacturing acceptance testing or for performing diagnostics on electronics within medical device 100. Alternatively or in addition, electrical connectors 108 may enable a subsystem to be electrically connected to a next level system. Medical device 100 may, in various cases, be the subsystem or the next level system.

Switch 114 may include, for example, a tactile switch, or a rubber dome with a conductive pad within the rubber dome. Switch 114 may be an interface that may enable a user to power on electronics in medical device including, for example, circuitry on circuit board 106. Alternatively or in addition, switch 114 may be an interface that enables a user to adjust parameters/settings, e.g., for physiological sensing and/or delivery of therapy, of the medical device 100.

Casing 102 may be configured to receive circuit board 106 with side 106a of circuit board 106 (the side including electrical connectors 108) facing casing 102. Casing 102 may be configured to surround at least a portion of circuit board 106. Casing 102 may define aperture 110 and aperture 110 may be configured to allow electrical connectors 108 of circuit board 106 to extend through aperture 110 to allow for one or more electrical connections between electrical connectors 108 of the circuit board 106 and one or more components outside of casing 102. The one or more components outside of casing 102 may include, for example, a programmer, a recharger, a communication device, such as a cradle, for connecting the medical device to one or more wired or wireless networks, a sensor actuator packet, electrodes, such as on an EMG (electromyogram) tube and/or on any other suitable component, and/or any other suitable components according to particular needs In some examples, medical device 100 may further include a fill material within casing 102 and forming an overmold 103 covering at least a portion of side 106*b* of circuit board 106. The fill material may cover at least a portion of side 106*a* of circuit board 106 and at least a portion of side 106*b* of circuit board 106. In some examples, the fill material does not extend over the first portion of outer surface 104 defined by casing 102. In some examples, because switch 114 may be substantially aligned with electrical connectors 108, switch 114 and one or more electrical connectors 108 may be used as clamping points during insertion of the fill material into casing 102. In some examples, casing 102 may comprise a material having a first melting temperature and the fill material may have a second melting temperature that is lower than the first melting temperature. Thus, the fill material may be inserted around circuit board 106 without melting casing 102 such that casing 102 may support circuit board 106 during insertion of the fill material such that heat and/or force applied to circuit board 106 during insertion of the fill material does not warp circuit board 106 or casing 102.

In some examples, first portion 104*a* of outer surface 104 defined by casing 102 may include one or more markings 115 indicating an identifier for casing 102 and/or medical device 100. Because the fill material does not cover first portion 104*a* of outer surface 104 defined by casing 102, markings 115 may remain exposed during and after assembly of medical device 100, which may allow for improved tracking of medical device 100 throughout and after assembly of medical device 100. In some examples, markings 115 may also include, for example, a logo and/or regulatory, standards, and/or instructional information.

In some examples, casing 102 may include one or more energy director features 116*a* and 116*b* (collectively "116") for plastic ultrasonic welding. For example, energy director features 116 may facilitate connecting casing 102 of medical device 100 to other elements by, for example, plastic ultrasonic welding. Casing 102 of medical device 100 may be welded to, for example, a next-level system or any other suitable element. Although energy director features 116 are illustrated as including two energy director features 116*a* and 116*b* each having a triangular prism shape, and each being located near a corner of casing 102, energy director features 116 may have any suitable configuration including any suitable number, size, shape, location, or any other suitable characteristics according to particular needs. In general, energy director features 116 are configured, e.g., shaped and/or sized, such that incident ultrasonic energy heats the features 116 so that the material of features may change shape and/or phase to facilitate connection of casing 102 with another element or system.

Medical device 100 may include any suitable components according to particular needs. For example, medical device 100 may include one or more power source, microprocessor, communication module, voltage regulator, oscillator, memory, capacitor, resistor, comparator, integrated circuit, electrode, antenna, inductor, sensor (e.g., a physical, electrical, and/or chemical sensor), printed circuit board, accelerometer, connector, sound generator such as a buzzer and/or speaker, chemical sensor, light emitting and/or receiving component, and/or display.

Although electrical connectors 108 and switch 114 are described as being electrical connectors and a switch, in some examples, they may be replaced and/or may additionally include any other suitable components including any of the components listed above. FIGS. 2A and 2B are conceptual perspective views of circuit board 106 of medical device 100 of FIGS. 1A-1D.

Circuit board 106 may be a printed circuit board assembly (PCBA) or any other suitable type of circuit board. As described above with reference to FIGS. 1A-1D, circuitry 202 on circuit board 106 may be configured to monitor a physiological parameter of a subject and/or control delivery of a therapy to the subject. Additionally, side 106*a* of circuit board 106 may include one or more electrical connectors 108 and side 106*b* of circuit board 106 may include switch 114. Circuit board 106 may include a battery 204. Although battery 204 is illustrated as being on side 106*a* of circuit board 106, battery 204 may be in any suitable location. Circuit board 106 may include a connecting mechanism 206 for connecting battery 204 to other elements of circuit board 106 which may include, for example, a pin-through-hole, a soldering pad, or a connector. In some examples, one or more of the electronic components of circuit board 106 may be mounted or placed directly on the surface of circuit board 106.

Figure 8:
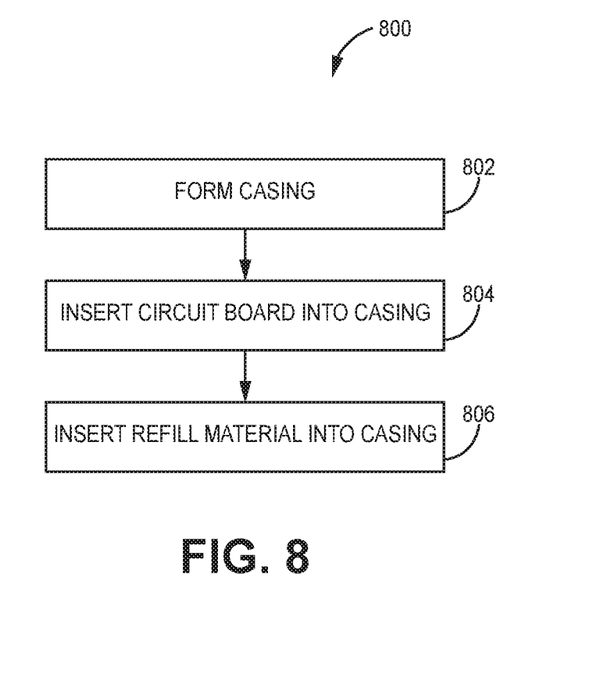
FIG. 8 is a flow chart diagram illustrating an example method of manufacture of the device shown in FIGS. 1A-1D.

FIGS. 3-7 are conceptual perspective views of components of medical device 100 in various stages of manufacture of medical device 100 shown in FIGS. 1A-1D. FIG. 8 is a flow chart diagram illustrating an example method of manufacture of the device shown in FIGS. 1A-1D.

Figure 3:
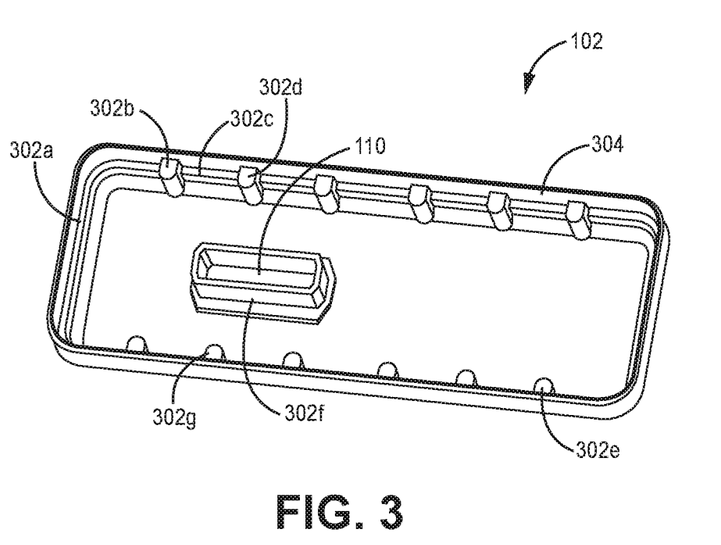
FIGS. 3-7 are conceptual perspective views of components of the medical device of FIGS. 1A-1D in various stages of manufacture of the medical device shown in FIGS. 1A-1D.

Casing 102 may be formed using any suitable technique (FIG. 3 showing an interior perspective view of casing 102; Step 802 of FIG. 8). For example, casing 102 may be formed using a molding process, a machining process, and/or any other suitable process according to particular needs. Casing 102 may define one or more internal structures 302 configured to support circuit board 106 after insertion of circuit board 106 into casing 102. Casing 102 may define an inner surface 304 and internal structures 302 may include one or more protrusions protruding inwardly from inner surface 304 of casing 102. In some examples, internal structures 302 may be configured to support circuit board 106 before insertion of fill material into casing 102. In some examples, internal structures 302 may be configured to maintain a gap between at least one portion of side 106*a* of circuit board 106 and at least one portion of casing 102 during insertion of the fill material to allow for at least some of the fill material to be placed between the portions of side 106*a* of circuit board 106 and of casing 102. In some examples, internal structures 302 may include an aperture wall 302*f* defining at least a portion of aperture 110. Internal structures 302 may provide certain advantages. For example, by supporting circuit board 106 before and during insertion of fill material, and by maintaining a preferred distance between one or more portions of circuit board 106 and casing 102, unwanted bending of circuit board 106 may be reduced or eliminated. Reducing or eliminating unwanted bending of circuit board 106 may help to prevent warpage of medical device 100 after inserting fill material into casing and over circuit board 106 and cooling of fill material.

Figure 4:
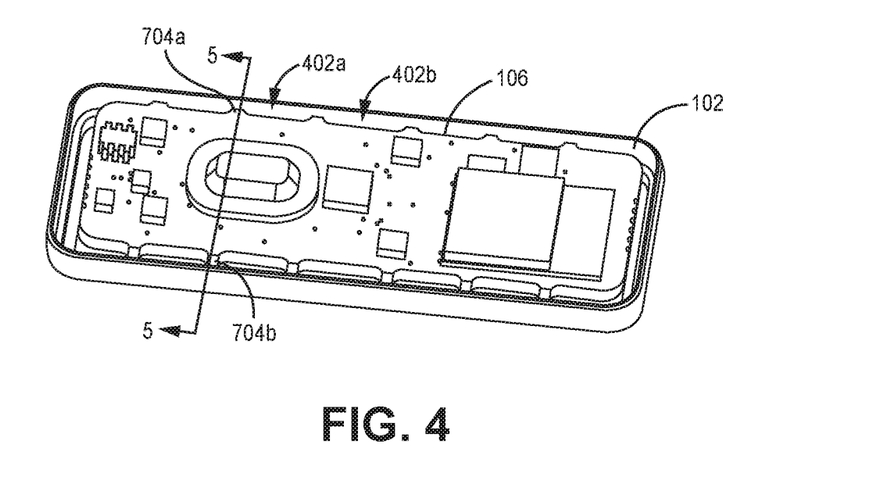
Figure 5:
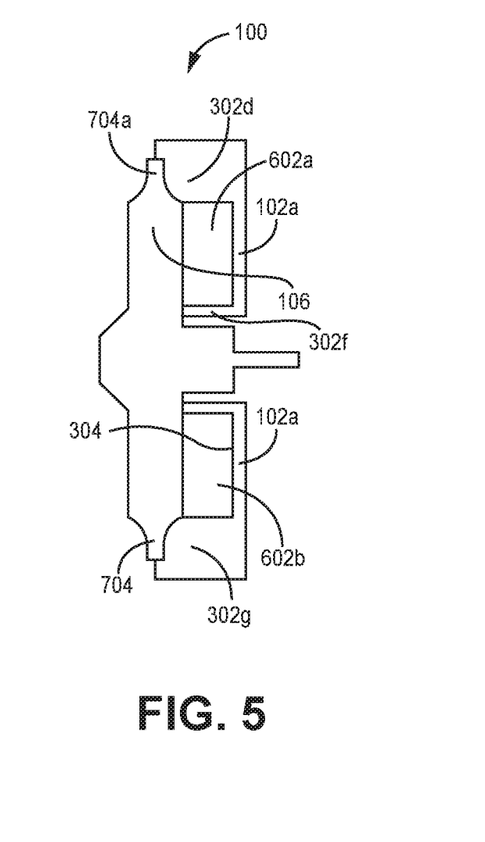
Figure 6:
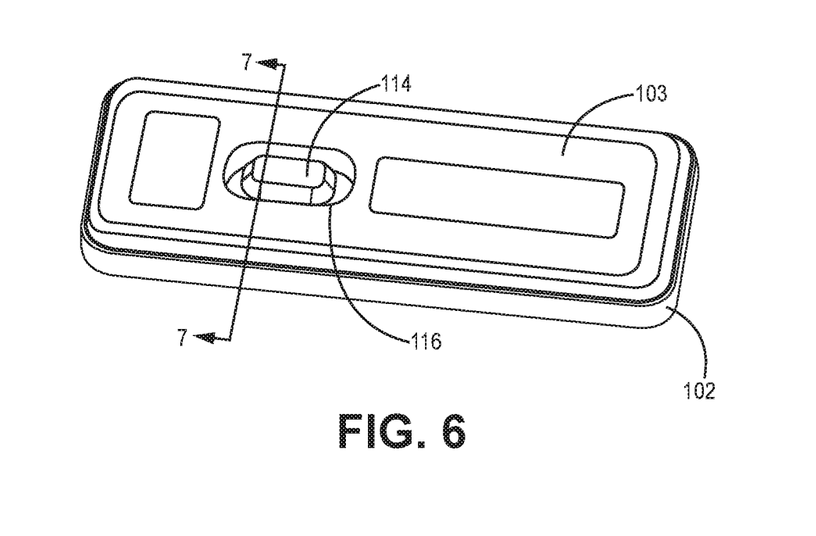
Figure 7:
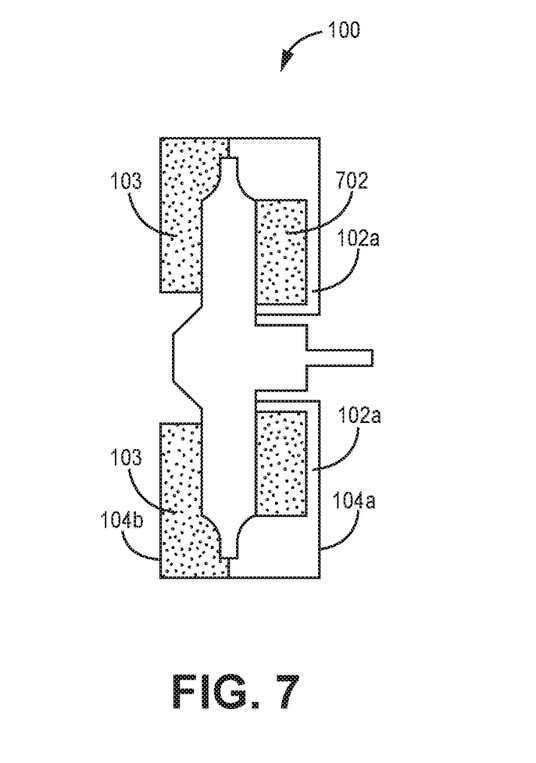

Circuit board 106 may be inserted into casing. FIG. 4 shows a perspective view of circuit board 106 inserted into casing 102. FIG. 5 shows a cross-sectional view of a portion of circuit board 106 within casing 102, taken along line 5-5 of FIG. 4, Step 804 of FIG. 8.). Circuit board 106 may be inserted into casing such that side 106a of circuit board 106 faces casing 102 (as shown in FIG. 5) and such that aperture 110 of casing 102 may allow electrical connectors 108 to extend throughout aperture 110 to allow for one or more electrical connections between one or more of electrical connectors 108 of circuit board 106 and one or more components outside of casing 102 (as shown in FIGS. 1A, 1C, and 5). Openings 402 between circuit board 106 and casing 102 may allow for insertion of fill material as described in further detail with reference to FIG. 5.

As shown in FIG. 5, casing 102 may define one or more internal structures 302 configured to support circuit board 106 after insertion of circuit board 106 into casing 102, including one or more protrusions protruding inwardly from inner surface 304 of casing 102. Internal structures 302 may support circuit board 106 before insertion of fill material into casing 102 and/or may be configured to maintain one or more gaps 602 between at least one portion of side 106a and/or side 106b of circuit board 106 and at least one portion of casing 102 during insertion of the fill material to allow for at least some of the fill material to be placed between the portions of side 106a and/or side 106b of circuit board 106 and of casing 102. In some examples, internal structures 302 may include an aperture wall 302f defining at least a portion of aperture 110.

In the cross-section shown in FIG. 5, internal structures 302d and 302g mate with respective tabs 704a and 704b of circuit board 106. However, at least some portions of the device 100 may not include internal structures 302 or tabs 704 so that, as shown in FIG. 4, one or more openings 402 are formed and may allow fill material to be inserted through openings in order to fill gaps 602 with fill material.

Fill material 702 may be inserted into casing 102 (FIGS. 6 and 7, Step 806 of FIG. 8), including within gaps 602 shown in FIG. 5, and over at least a portion of side 106b of circuit board 106 to form overmold 103. Fill material 702 may include, for example, injection molded plastic and/or adhesive. In some examples, fill material 702 may include thermoplastic elastomers (TPE) such as styrene ethylene butylene styrene copolymer (SEBS), polypropylene, polycaprolactone, polystyrene, high impact polystyrene, maleated polypropylene, ethylene vinyl acetate (EVA), polyolefin (POE), polyamide, high flow thermoplastic polyurethane (TPU), epoxy, silicone, polyurethane-silicone copolymer, or any other suitable material. In some examples, fill material 702 may inserted into casing 102 and/or over side 106b of circuit board 106 at a temperature below 425° F.

As shown, in some examples, fill material 702 does not extend over first portion 104a, defined by casing 102, of outer surface 104 of medical device 100. Thus, casing 102 may define a first portion 104a of the outer surface 104 of medical device 100 such that an outer surface of casing 102 is also a first portion 104a of an outer surface 104 of medical device 100, which may provide certain advantages. For example, markings such as marking 115 shown in FIGS. 1A and 1C of casing 102, may remain on the outer surface 104 of medical device 100 such that it is visible during and after assembly of medical device 100, which may assist in tracking medical device 100 throughout and after the assembly process. Additionally, because fill material 702 does not extend over the first portion 104a of outer surface 104 defined by casing 102 such that casing 102 defines the first portion 104a the outer surface 104 of medical device 100, medical device 100 may be more water resistant, water proof, and/or more durable than a device in which fill material covers a substantial portion of casing 102. Additionally, manufacturing medical device 100 may be less expensive that manufacturing a device in which additional elements or more costly fill material is required to make the device sufficiently water resistant, water proof, and/or durable.

Various examples have been described. These and other examples are within the scope of the following claims.

What is claimed is:

1. A medical device, comprising:
   a circuit board having a first side and a second side opposite the first side, the first side including one or more electrical connectors;
   circuitry on the circuit board configured to at least one of monitor a physiological parameter of a subject or control delivery of a therapy to the subject;
   a casing, the casing configured to receive the circuit board with the first side of the circuit board facing the casing and surround at least a portion of the circuit board, the casing defining an aperture configured to allow the one or more electrical connectors to extend through the aperture for one or more electrical connections between the one or more electrical connectors of the circuit board and one or more components outside of the casing, an outer surface of the casing defining a first portion of an outer surface of the medical device, the casing comprising a material having a first melting temperature; and
   a fill material, at least a portion of the fill material being within the casing, the fill material covering at least a portion of the first side of the circuit board and at least a portion of the second side of the circuit board, the fill material defining a second portion of the outer surface of the medical device, and the fill material having a second melting temperature that is lower than the first melting temperature.

2. The medical device of claim 1, wherein the casing defines one or more internal structures configured to support the circuit board after insertion of the circuit board into the casing.

3. The medical device of claim 2, wherein the one or more internal structures comprise one or more protrusions protruding inwardly from an inner surface of the casing.

4. The medical device of claim 2, wherein the one or more internal structures are configured to support the circuit board before insertion of the fill material into the casing.

5. The medical device of claim 4, wherein the one or more internal structures are configured to maintain a gap between at least one portion of the first side of the circuit board and at least one portion of the casing during insertion of the fill material to allow for at least some of fill material to be placed between the at least one portion of the first side of the circuit board and the at least one portion of the casing.

6. The medical device of claim 2, wherein the one or more internal structures comprise an aperture wall defining at least a portion of the aperture.

7. The medical device of claim 1, wherein the casing is formed using a molding process.

8. The medical device of claim 1, wherein the casing is formed using a machining process.

9. The medical device of claim 1, wherein the fill material does not extend outside the casing.

10. The medical device of claim 1, wherein the outer surface of the casing includes one or more markings indicating an identifier for the casing.

11. The medical device of claim 1, further comprising a switch on the second side of the circuit board.

12. The medical device of claim 10, wherein the switch is substantially aligned with the one or more electrical connectors.

13. The medical device of claim 12, wherein one or more of the switch or the one or more electrical connectors are used as a clamping point during insertion of the fill material into the casing.

14. The medical device of claim 1, wherein the one or more electrical connectors comprise one or more pin connectors.

15. A method of manufacturing a medical device comprising a circuit board, circuitry on the circuit board, a casing and a fill material, the method comprising:
inserting the circuit board into the casing, the circuit board having a first side and a second side opposite the first side, the first side including one or more electrical connectors, circuitry on the circuit board configured to monitor a physiological parameter of a subject or control delivery of a therapy to the subject, the casing configured to receive the circuit board with the first side of the circuit board facing the casing and surround at least a portion of the circuit board, the casing defining an aperture configured to allow the one or more electrical connectors to extend through the aperture for one or more electrical connections between the one or more electrical connectors of the circuit board and one or more components outside of the casing, an outer surface of the casing defining a first portion of an outer surface of the medical device, the casing comprising a material having a first melting temperature; and
inserting a at least a portion of a fill material into the casing, wherein the fill material does not extend over the outer surface the casing, the fill material defining a second portion of the outer surface of the medical device, and the fill material having a second melting temperature that is lower than the first melting temperature.

16. The method of claim 15, further comprising forming the casing.

17. The method of claim 16, wherein forming the casing comprises forming the casing using a molding process.

18. The method of claim 16, wherein forming the casing comprises forming the casing using a machining process.

19. The method of claim 15, wherein the casing comprises one or more internal structures configured to support the circuit board after insertion of the circuit board into the casing.

20. The method of claim 19, wherein the one or more internal structures comprise one or more protrusions protruding inwardly from an inner surface of the casing.

21. The method of claim 20, wherein the one or more internal structures are configured to support the circuit board before insertion of the fill material into the casing.

22. The method of claim 15, wherein the outer surface of the casing comprises one or more markings indicating an identifier for the casing.

23. A medical device, comprising:
a circuit board having a first side and a second side opposite the first side, the first side including one or more electrical connectors;
circuitry on the circuit board configured to at least one of monitor a physiological parameter of a subject or control delivery of a therapy to the subject;
a casing, the casing configured to receive the circuit board with the first side of the circuit board facing the casing and surround at least a portion of the circuit board, the casing defining an aperture configured to allow the one or more electrical connectors to extend through the aperture for one or more electrical connections between the one or more electrical connectors of the circuit board and one or more components outside of the casing, an outer surface of the casing defining a first portion of an outer surface of the medical device, the casing defining one or more protrusions protruding inwardly from an inner surface of the casing and configured to support the circuit board after insertion of the circuit board into the casing and before insertion of a fill material within the casing, the casing comprising a material having a first melting temperature; and
the fill material, at least a portion of the fill material being within the casing, the fill material covering at least a portion of the first side of the circuit board and at least a portion of the second side of the circuit board, the fill material defining a second portion of the outer surface of the medical device, and the fill material having a second melting temperature that is lower than the first melting temperature.

* * * * *